United States Patent
Keiser et al.

(10) Patent No.: US 10,376,289 B2
(45) Date of Patent: *Aug. 13, 2019

(54) CROSS CONNECTOR SYSTEM

(71) Applicant: Zimmer Biomet Spine, Inc., Westminster, CO (US)

(72) Inventors: Matthew L Keiser, Hillsdale, NJ (US); Laurie G Sanders, Glen Ridge, NJ (US); Scott Harrington, San Jose, CA (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/832,149

(22) Filed: Dec. 5, 2017

(65) Prior Publication Data

US 2018/0092668 A1    Apr. 5, 2018

Related U.S. Application Data

(63) Continuation of application No. 14/253,917, filed on Apr. 16, 2014, now Pat. No. 9,855,079.

(Continued)

(51) Int. Cl.
*A61B 17/70* (2006.01)

(52) U.S. Cl.
CPC ...... *A61B 17/7052* (2013.01); *A61B 17/7032* (2013.01); *A61B 17/705* (2013.01); *A61B 17/7037* (2013.01); *A61B 17/7049* (2013.01)

(58) Field of Classification Search
CPC ............ A61B 17/7052; A61B 17/7049; A61B 17/705
See application file for complete search history.

(56) References Cited

U.S. PATENT DOCUMENTS

| 5,501,684 | A | 3/1996 | Schlapfer et al. |
| 7,645,294 | B2 | 1/2010 | Kalfas et al. |

(Continued)

FOREIGN PATENT DOCUMENTS

| EP | 2455031 A2 | 5/2012 |
| WO | WO-2010065795 A1 | 6/2010 |
| WO | WO-2014172445 A1 | 10/2014 |

OTHER PUBLICATIONS

"U.S. Appl. No. 14/253,917, Final Office Action dated Dec. 15, 2016", 8 pgs.
"U.S. Appl. No. 14/253,917, Non Final Office Action dated Jun. 7, 2016", 9 pgs.
"U.S. Appl. No. 14/253,917, Notice of Allowance dated Feb. 14, 2017", 7 pgs.

(Continued)

*Primary Examiner* — Ellen C Hammond
(74) *Attorney, Agent, or Firm* — Schwegman Lundberg & Woessner, P.A.

(57) ABSTRACT

The present teachings provide one or more surgical implements for repairing damaged tissue, such as in the case of a spinal fixation procedure. A cross connector system for use during a spinal fixation procedure is provided. The system includes at least one bridge defining a coupling bore and having a pair of downwardly extending arms for coupling to a first bone engaging member. The system includes a contoured bar having a first end offset from a second end, and a bore having a central axis. The system includes an expansion ring received within the bore, and a locking device received through the expansion ring and the coupling bore. The locking device is operable in a first state in which the contoured bar is movable about the central axis of the bore and in a second state in which the contoured bar fixed relative to the central axis of the bore.

24 Claims, 5 Drawing Sheets

Related U.S. Application Data

(60) Provisional application No. 61/812,870, filed on Apr. 17, 2013.

(56) References Cited

U.S. PATENT DOCUMENTS

| | | |
|---|---|---|
| 8,070,775 B2 | 12/2011 | Winslow et al. |
| 8,197,515 B2 | 6/2012 | Levy |
| 8,672,978 B2 | 3/2014 | Dant et al. |
| 8,870,923 B2 | 10/2014 | Richelsoph |
| 8,920,475 B1 | 12/2014 | Ziemek et al. |
| 9,198,696 B1 | 12/2015 | Bannigan et al. |
| 9,220,541 B1 | 12/2015 | Dant et al. |
| 9,247,964 B1 | 2/2016 | Shoshtaev |
| 9,855,079 B2 | 1/2018 | Keiser et al. |
| 2003/0028192 A1 | 2/2003 | Schar |
| 2006/0217718 A1 | 9/2006 | Chervitz et al. |
| 2007/0219556 A1 | 9/2007 | Altarac et al. |
| 2008/0221622 A1 | 9/2008 | Triplett et al. |
| 2009/0177234 A1 | 7/2009 | Butler et al. |
| 2009/0264931 A1 | 10/2009 | Miller et al. |
| 2010/0160981 A1 | 6/2010 | Butler et al. |
| 2010/0204733 A1 | 8/2010 | Rathbun et al. |
| 2011/0046675 A1* | 2/2011 | Barrus ............... A61B 17/7052 606/252 |
| 2011/0112578 A1 | 5/2011 | Keiser et al. |
| 2012/0226316 A1 | 9/2012 | Dant et al. |
| 2013/0006306 A1 | 1/2013 | Saidha et al. |
| 2014/0316468 A1 | 10/2014 | Keiser et al. |

OTHER PUBLICATIONS

"U.S. Appl. No. 14/253,917, Notice of Allowance dated Sep. 15, 2017", 8 pgs.

"U.S. Appl. No. 14/253,917, Response filed Feb. 2, 2017 to Final Office Action dated Dec. 15, 2016", 11 pgs.

"U.S. Appl. No. 14/253,917, Response filed Feb. 22, 2016 to Restriction Requirement dated Jan. 15, 2016", 9 pgs.

"U.S. Appl. No. 14/253,917, Response filed Sep. 7, 2016 to Non Final Office Action dated Jun. 7, 2016", 15 pgs.

"U.S. Appl. No. 14/253,917, Restriction Requirement dated Jan. 15, 2016", 6 pgs.

"European Application Serial No. 14786045.6, Extended European Search Report dated Dec. 14, 2016", 10 pgs.

"European Application Serial No. 14786045.6, Response filed Jun. 6, 2016 to Communication pursuant to Rules 161(1) and 162 EPC dated Dec. 15, 2015", 12 pgs.

"European Application Serial No. 14786045.6, Response filed Jul. 20, 2017 to Extended European Search Report dated Dec. 14, 2016", 23 pgs.

"International Application Serial No. PCT/US2014/034340, International Preliminary Report on Patentability dated Oct. 29, 2015", 8 pgs.

"International Application Serial No. PCT/US2014/034340, International Search report dated Aug. 14, 2014", 3 pgs.

"International Application Serial No. PCT/US2014/034340, Written Opinion dated Aug. 14, 2014", 6 pgs.

* cited by examiner

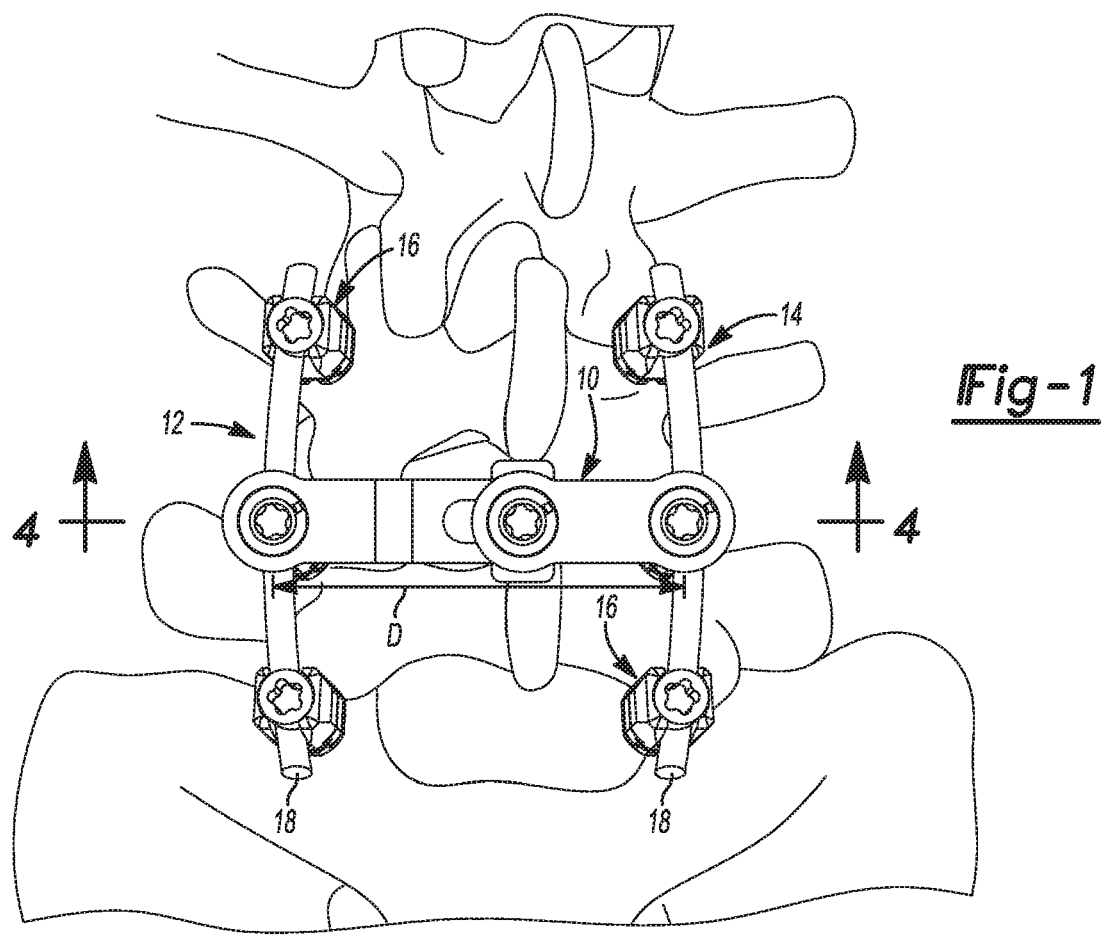
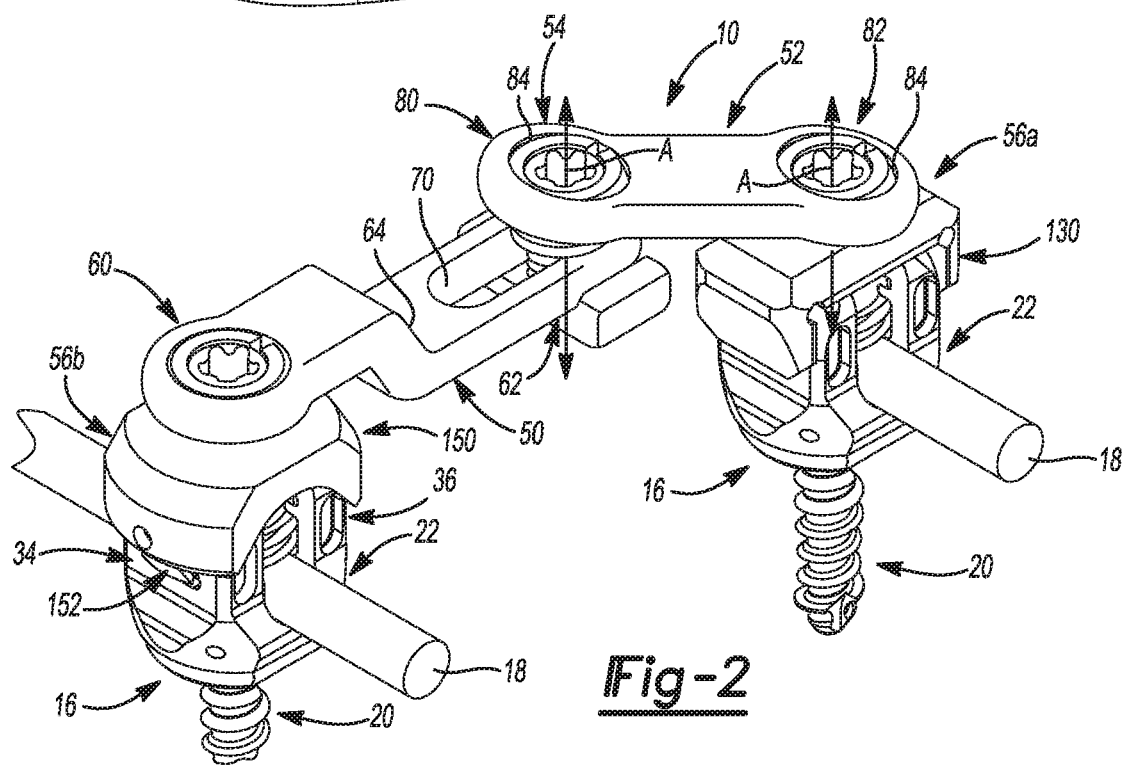

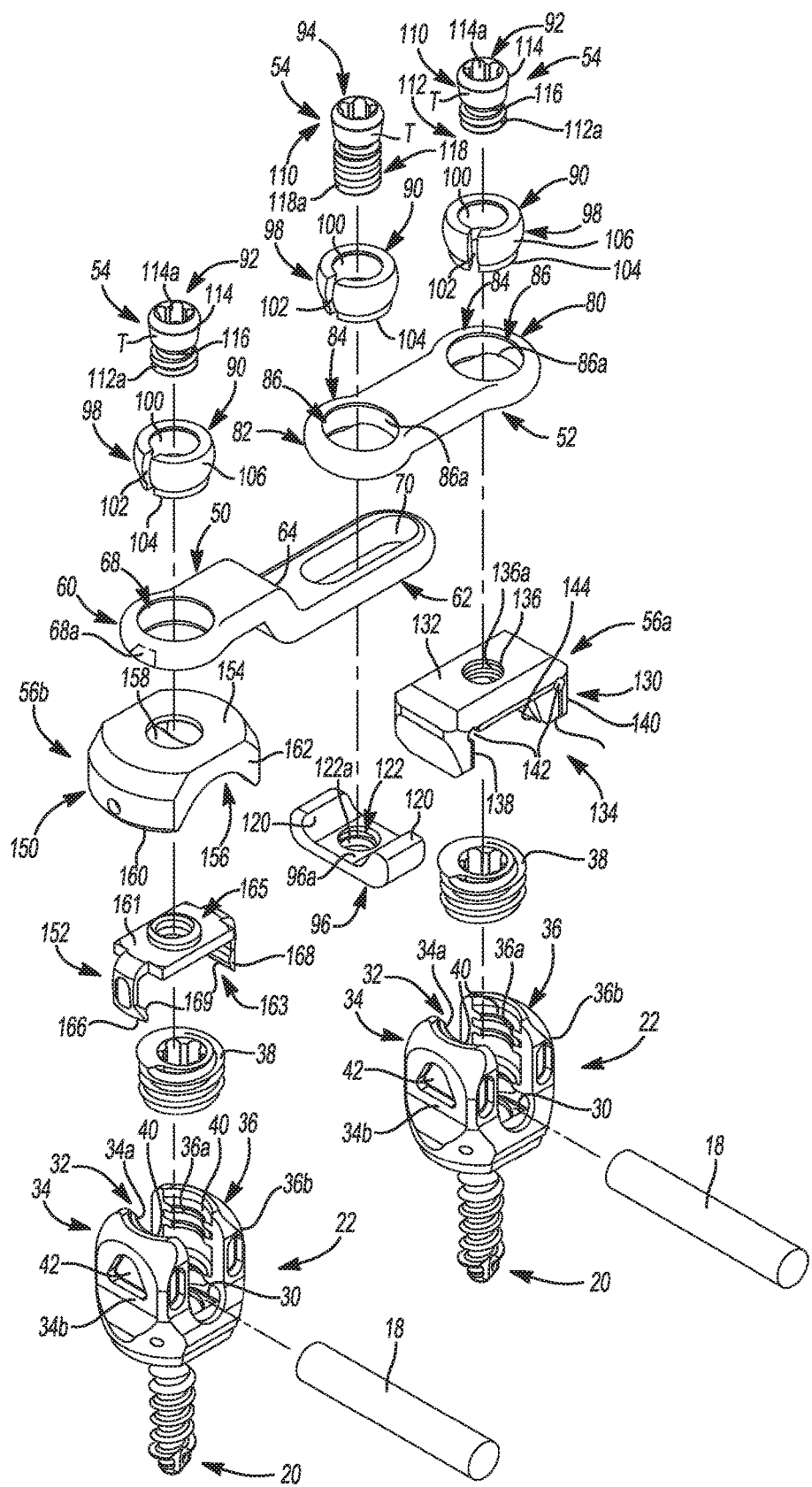

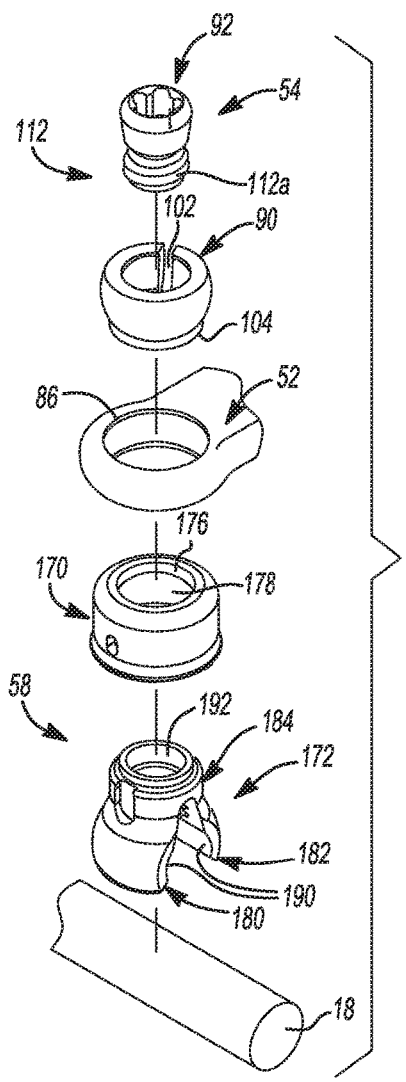
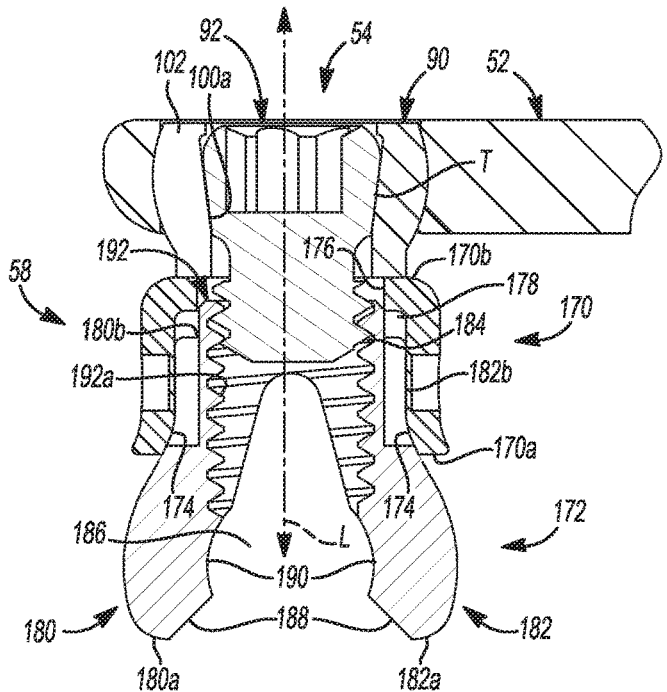
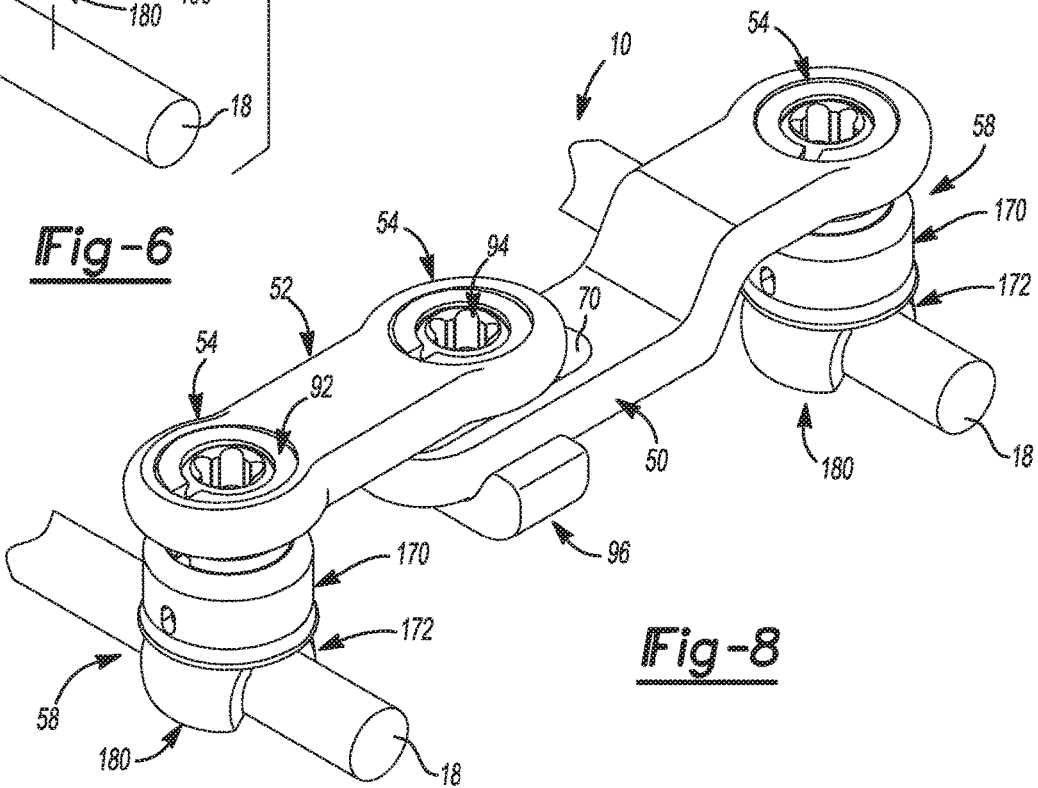
Fig-6
Fig-7
Fig-8

CROSS CONNECTOR SYSTEM

CROSS-REFERENCE TO RELATED APPLICATIONS

This application is a continuation of U.S. patent application Ser. No. 14/253,917, filed on Apr. 16, 2014, which issued as U.S. Pat. No. 9,855,079 on Jan. 2, 2018, which claims the benefit of U.S. Provisional Application No. 61/812,870, filed on Apr. 17, 2013. The entire disclosure of the above applications are incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc., to restore function to the damaged tissue.

Generally, in order to stabilize various boney tissue relative to one another, such as vertebrae of the spine, one or more implants can be coupled to each of the vertebrae and interconnected via a suitable device. In one example, implants or anchors can be coupled to each of the vertebrae, and a connecting device, such as a rod, can be coupled to each of the anchors to stabilize or fix the vertebrae relative to each other. In certain instances, it may be desirable to attach multiple anchors to each vertebrae on opposite sides of the spinous process so that multiple rods can be used to stabilize or fix the vertebrae relative to each other. When multiple rods and anchors are employed in a surgical procedure, it may be desirable to provide a cross connector to interconnect the rods or anchors to impart additional stability and strength to the anchor and rod assemblies. The present teachings can provide a cross connector for use in a fixation procedure, such as a spinal fixation procedure, which can interconnect multiple anchor and rod assemblies.

SUMMARY

Provided is a cross connector system for use during a spinal fixation procedure. The system can include at least one bridge defining a coupling bore and having a pair of downwardly extending arms adapted to be coupled to a first bone engaging member. The system can also include a contoured bar having a first end offset from a second end. The first end of the contoured bar can define a bore having a central axis. The system can include an expansion ring received within the bore of the contoured bar, and a locking device received through the expansion ring and the coupling bore for coupling the at least one bridge to the contoured bar. The locking device can be operable in a first state in which the contoured bar is movable about the central axis of the bore and in a second state in which the contoured bar is fixed relative to the central axis of the bore so as to fixedly couple the at least one bridge to the contoured bar.

Further provided is a cross-connector system for use during a spinal fixation procedure. The system can include at least one bridge defining a throughbore and having a first pair of downwardly extending arms. The system can also include a clamp having a coupling bore and a second pair of downwardly extending arms. The clamp can be positionable adjacent to the at least one bridge such that the throughbore of the at least one bridge is aligned with the coupling bore of the clamp. The clamp is adapted to be coupled to a first bone engaging member. The system can also include at least one bar having a first end defining a bore, and an expansion ring received within the bore of the bar. The system can include a locking device received through the expansion ring, the throughbore of the at least one bridge and the coupling bore of the clamp for coupling the at least one bridge to the bar.

Also provided is a cross-connector system for use during a spinal fixation procedure. The system can include a first bridge defining a first coupling bore and having a first pair of downwardly extending arms adapted to be coupled to a first bone engaging member. The system can also include a second bridge defining a second coupling bore and having a second pair of downwardly extending arms adapted to be coupled to a second bone engaging member. The system can include a linkage system having a first end defining a first bore having an axis and a second end defining a second bore having an axis. The system can also include a first expansion ring received within the first bore of the linkage system, and a second expansion ring received within the second bore of the linkage system. The system can include a first locking device received through the first expansion ring and the first coupling bore of the first bridge to couple the first bridge to the first end of the linkage. A second locking device can be received through the second expansion ring and the second coupling bore of the second bridge to couple the second bridge to the second end of the linkage.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 1 is a schematic environmental illustration of an exemplary cross connector system for use in a spinal fixation procedure according to the present teachings.

FIG. 2 is a perspective illustration of the exemplary cross connector system of FIG. 1.

FIG. 3 is an exploded view of the exemplary cross connector system of FIG. 2.

FIG. 6 is an exploded view of the exemplary cross connector system of FIG. 5.

FIG. 7 is a cross-sectional view of the exemplary cross connector system of FIG. 5, taken along line 7-7 of FIG. 5.

FIG. 8 is a perspective illustration of yet another exemplary cross connector system for use in a spinal fixation procedure according to the present teachings.

DESCRIPTION OF VARIOUS ASPECTS

Figure 4:
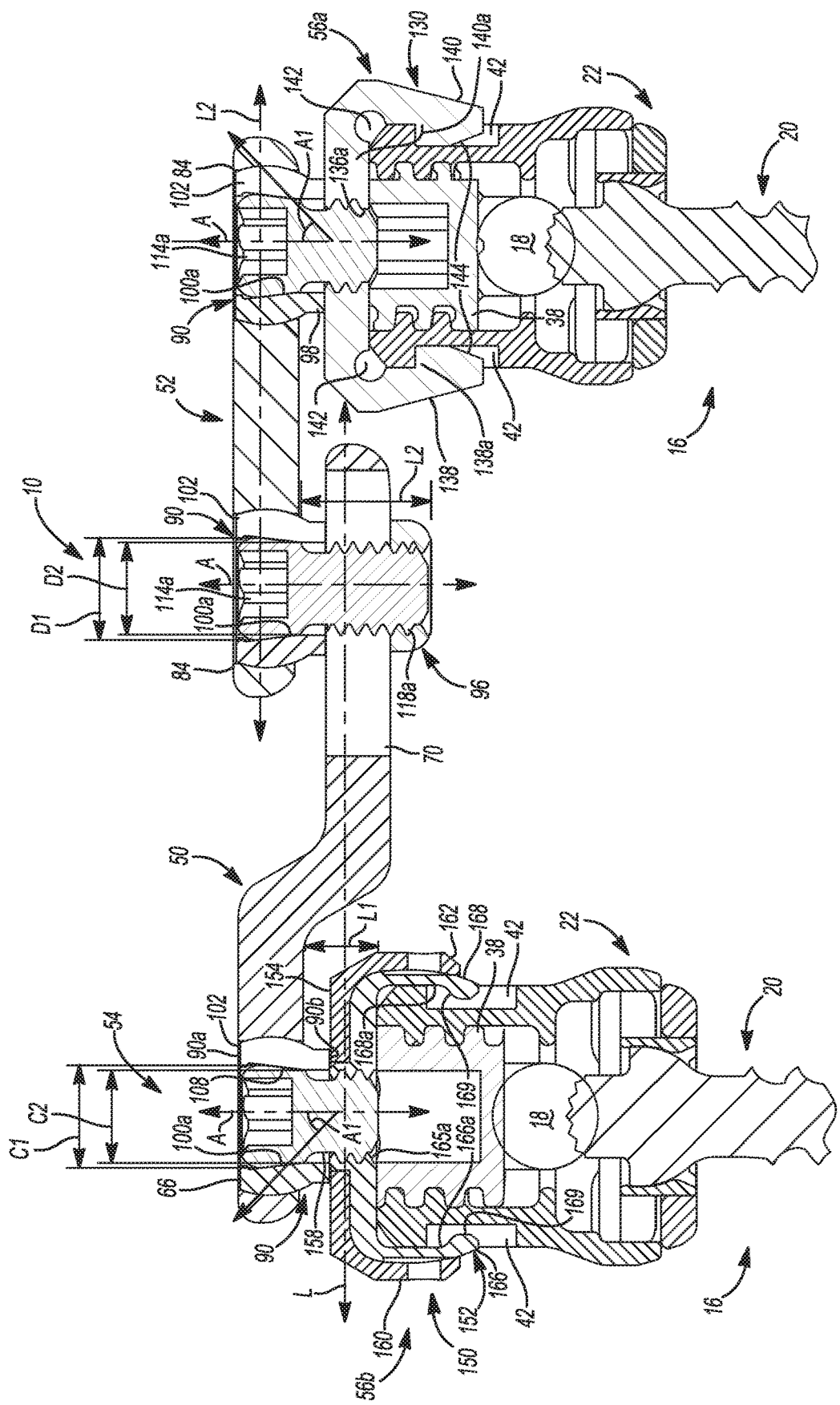
FIG. 4 is a cross-sectional view of the exemplary cross connector system of FIG. 1, taken along line 4-4 of FIG. 1.

The following description is merely exemplary in nature and is not intended to limit the present teachings, application, or uses. It should be understood that throughout the drawings, corresponding reference numerals indicate like or corresponding parts and features. Although the following description is related generally to a cross connector system for use in an anatomy to strengthen a construct formed by one or more spinal fixation systems, such as in the case of spinal fusion, static spinal stabilization or dynamic spinal stabilization, it will be understood that the system as described and claimed herein can be used in any appropriate surgical procedure, such as in a minimally invasive orthopedic alignment or fixation procedure. Therefore, it will be understood that the following discussions are not intended to limit the scope of the present teachings and claims herein.

With reference to FIGS. 1-8, a cross connector system 10 is shown. The cross connector system 10 may be particularly adapted for spinal fixation procedures. Various aspects of the present teachings, however, may have application for other procedures. In certain applications, the cross connector system 10 can be used to interconnect a first spinal fixation system 12 with a second spinal fixation system 14. By connecting the first fixation system 12 to the second fixation system 14 with the cross connector system 10, forces acting on the first fixation system 12 can be distributed over the second fixation system 14, and vice versa. Thus, the cross connector system 10 can provide the first fixation system 12 and second fixation system 14 with additional strength and stability.

In one example, as illustrated in FIGS. 1 and 2, each of the first fixation system 12 and the second fixation system 14 can include a one or more bone engaging members 16, which can be interconnected via an elongated member or connecting rod 18. The bone engaging members 16 can comprise any suitable device, such as a spinal hook or bone anchor, that is capable of coupling to a portion of a vertebrae. The connecting rod 18 can comprise any suitable device capable of interconnecting the bone engaging members 16. For example, the first fixation system 12 and second fixation system 14 can be composed of spinal hooks, bone anchors and connecting rods, which are commercially available from Biomet, Inc. of Warsaw, Ind. In one example, the first fixation system 12 and the second fixation system 14 can comprise bone engaging members 16 and connecting rod(s) 18 selected from one or more of the POLARIS™ Deformity System, POLARIS™ 5.5 or 6.35 Spinal System, or ARRAY® Spinal System, each of which are commercially available from Biomet, Inc. of Warsaw, Ind.

In addition to or in the alternative, the bone engaging members 16 can comprise those disclosed in commonly owned U.S. patent application Ser. No. 12/614,734, filed on Nov. 9, 2009 and entitled "Multiplanar Bone Anchor System," and/or those disclosed in commonly owned U.S. patent application Ser. No. 13/103,069, filed on May 8, 2011 and entitled "Multiplanar Bone Anchor System," each of which are incorporated herein by reference. The bone engaging members 16 could also comprise one or more of the bone anchors disclosed in commonly owned U.S. patent application Ser. No. 12/688,013, filed on Jan. 15, 2010 and/or commonly owned U.S. patent application Ser. No. 12/842,556, filed on Jul. 23, 2010, each entitled "Uniplanar Bone Anchor" and each incorporated herein by reference.

As the bone engaging members 16 and connecting rod(s) 18 can be generally known, the bone engaging members 16 and connecting rod(s) 18 will not be discussed in great detail herein. Briefly, however, with reference to FIGS. 2 and 3, the bone engaging members 16 can each comprise a bone fastener 20 and a saddle 22. It should be noted, however, that the bone engaging members 16 could comprise a saddle with threads that engage the anatomy, spinal hooks, or any other suitable bone engaging device. The bone fastener 20 can have a shank 24 at a distal end and a head 26 at a proximal end. The shank 24 can be configured to couple the bone engaging member 16 to the anatomy, and the head 26 can couple the bone fastener 20 to the saddle 22.

With reference to FIG. 3, the saddle 22 can be generally U-shaped, and can include a seat 30 and a receiving portion 32. The seat 30 can be configured to receive the head 26 of the bone fastener 20. Generally, the seat 30 can be configured to enable or restrict the motion of the bone fastener 20 relative to the saddle 22, as is generally known. The receiving portion 32 can include a pair of upwardly extending arms 34, 36, which can cooperate with the seat 30 to define the U-shape. The upwardly extending arms 34, 36 can each have an interior surface 34a, 36a and an exterior surface 34b, 36b. The interior surface 34a, 36a can be configured to receive a fastener, such as a plug 38, which can be used to couple the rod 18 to the bone engaging member 16. Thus, each interior surface 34a, 36a can define a plurality of threads 40, which can mate with the plug 38 to couple the connecting rod 18 to the saddle 22. Each exterior surface 34b, 36b can include at least one coupling feature 42 for coupling the saddle 22 to a portion of the cross connector system 10 (FIG. 4). In one example, the at least one coupling feature 42 can include a triangular depression or detent, however, it will be understood that any suitable technique could be employed to couple the saddle 22 to the cross connector system 10, as will be discussed in greater detail herein.

With reference to FIGS. 2 and 3, the connecting rod 18 can be received within the cavity defined by the upwardly extending arms 34, 36 of the saddle 22. The connecting rod 18 can be coupled to the saddle 22 via a suitable mechanical fastener, such as the plug 38. An exemplary connecting rod 18 and plug 38 can be substantially similar to the connecting rod and plug employed in the Polaris™ 5.5 Spinal System, commercially available from Biomet, Inc. of Warsaw, Ind., or the connecting element disclosed in commonly owned U.S. Patent Publication No. 2008/0077138, filed on Apr. 20, 2007 and incorporated by reference herein. As the connecting rod 18 and the plug 38 can be generally known, the connecting rod 18 and plug 38 will not be discussed in great detail herein.

Briefly, however, the connecting rod 18 can comprise an elongated solid cylinder. The connecting rod 18 can also include a slight curvature, which can correspond to the natural curvature of the spine. Typically, the connecting rod 18 can be composed of a suitable biocompatible material having sufficient rigidity to fix the vertebral bodies V relative to each other. The plug 38 can include threads, which can matingly engage the plurality of threads 40 formed on the upwardly extending arms 34, 36 of the saddle 22.

It should be noted, however, that although the cross connector system 10 is generally illustrated and described herein as for use with the first fixation system 12 and the second fixation system 14, which each include bone engaging members 16 and connecting rods 18, the cross connector system 10 can be used with any combination of bone engaging members 16 and connecting rods 18 employed during a surgical procedure. In addition, the bone engaging members 16 need not be coupled to adjacent vertebral bodies V, but rather, the bone engaging members 16 can be positioned so as to skip adjacent vertebral bodies V, if desired. Further, the cross connector system 10 can be used with any combination of fixation elements, not limited to just those illustrated herein. For example, the cross connector system 10 could be employed to connect adjacent fixation plates together.

Figure 5:
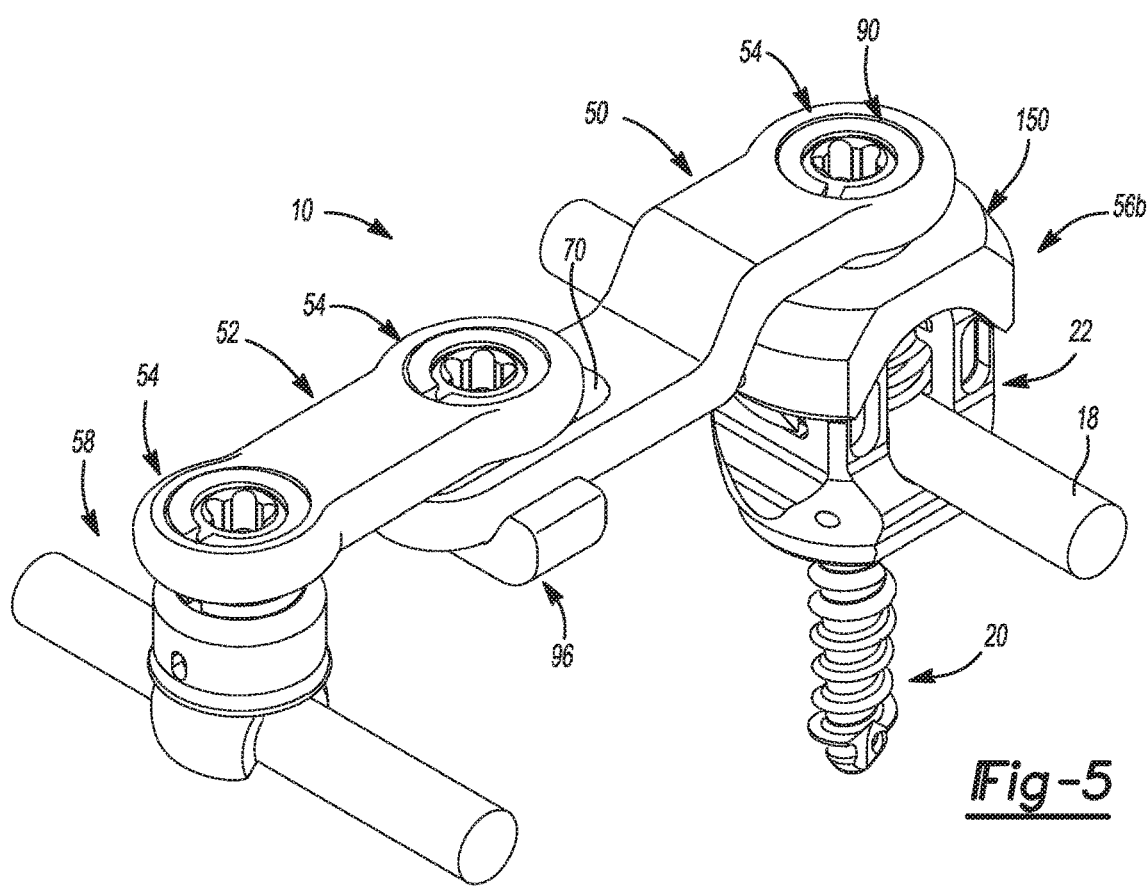
FIG. 5 is a perspective illustration of another exemplary cross connector system for use in a spinal fixation procedure according to the present teachings.

With reference to FIGS. 1-4, the cross connector system 10 can include a first or contoured bar 50, a second or planar bar 52, a locking system 54, a bridge system 56 and a rod clamp system 58 (FIG. 5). As will be discussed, any combination of the components of the cross connector system 10 can be used to interconnect the first fixation system 12 and the second fixation system 14 (FIG. 1). For example, the contoured bar 50 and the planar bar 52 can cooperate to form a linkage system, which can span a distance D between the first fixation system 12 and the second fixation system 14. In effect, the cross connector system 10 can be provided as a kit to enable the surgeon to configure the cross connector system 10 as needed for the particular patient's anatomy and fixation system employed. It should be noted that the distance D illustrated herein is merely exemplary, as the cross connector system 10 could be used to span any desired distance between the first fixation system 12 and second fixation system 14, which need not be a substantially horizontal distance.

With reference to FIG. 1, the contoured bar 50 can be used to at least partially span the distance D between the first fixation system 12 and the second fixation system 14. The contoured bar 50 can be composed of any suitable material, and for example, can be composed of a biocompatible metal, metal alloy or polymer. With reference to FIGS. 2-4, the contoured bar 50 can include a first or proximal end 60 and a second or distal end 62. It should be noted that the planar bar 52 can have any desired cross-sectional geometry, such as square, circular, oval, triangular, U-shaped, etc. Generally, the proximal end 60 can be offset from the distal end 62 relative to a longitudinal axis L defined by the contoured bar 50 (FIG. 4). In this regard, the contoured bar 50 can include a contour or slope 64 that transitions the proximal end 60 to the distal end 62. The slope 64 can allow the contoured bar 50 to pass through the patient's anatomy with minimal trauma while still adjusting the distance D as desired. It should be noted, however, that although the contoured bar 50 is described and illustrated herein as including the slope 64, the contoured bar 50 could be planar if desired, such that the proximal end 60 lies in the same plane as the distal end 62. Further, the contoured bar 50 could have any desired shape, such as linear or non-linear, and could be curved between the proximal and distal ends 60, 62 thereof.

With reference to FIGS. 3 and 4, the proximal end 60 can define a bore 66. The bore 66 can receive a portion of the locking system 54 to couple the proximal end 60 of the contoured bar 50 to one of the planar bar 52, bridge system 56 or rod clamp system 58. As will be discussed, the bore 66 can allow the locking system 54 to move relative to the bore 66. For example, the bore 66 can allow the locking system 54 to rotate about a main axis A of the bore 66 and pivot or angulate relative to the axis A when the locking system 54 is in a first state (FIG. 4). The bore 66 can have any desired shape, and for example, can be circular, elliptical, polygonal, etc.

With reference to FIGS. 3 and 4, the bore 66 can have an interior surface 68. The interior surface 68 can be configured to correspond to a portion of the locking system 54, as will be discussed in greater detail herein. In one example, the interior surface 68 can be spherical, however, the interior surface 68 can have any desired profile, such as smooth, spherical, tapered, etc. In addition, if desired, the internal surface 68 can include a maximum angle portion 68a. The maximum angle portion 68a can comprise a portion of the interior surface 68 of the bore 66 that has a reduced cross-section to enable the locking system 54 to pivot or angulate relative to the axis A to another, greater, maximum angle A1 as illustrated in FIG. 4.

The distal end 62 of the contoured bar 50 can define a slot 70. The slot 70 can generally be defined between the distal end 62 and the slope 64. It should be noted that although the distal end 62 is described and illustrated herein as including the slot 70, the distal end 62 could also include the bore 66, if desired. The slot 70 can receive a portion of the locking system 54 to couple the distal end 62 of the contoured bar 50 to one of the planar bar 52, bridge system 56 or rod clamp system 58. As will be discussed, the slot 70 can allow the locking system 54 to move or translate, rotate and pivot or angulate relative to the slot 70 when the locking system 54 is in a first state. By allowing the locking system 54 to move linearly or translate within the slot 70, a length of the cross connector system 10 can be adjusted as needed to fit the distance D between the first fixation system 12 and second fixation system 14.

With reference to FIGS. 1-4, the planar bar 52 can be used with the contoured bar 50 to at least partially span a distance D between the first fixation system 12 and the second fixation system 14. The planar bar 52 can be composed of any suitable material, and for example, can be composed of a biocompatible metal, metal alloy or polymer. The planar bar 52 can include a first or proximal end 80 and a second or distal end 82. It should be noted that the planar bar 52 can have any desired cross-sectional geometry, such as square, circular, oval, triangular, U-shaped, etc. Generally, the proximal end 80 can be planar with the distal end 82. In other words, the planar bar 52 can define a longitudinal axis L2, and the proximal end 80 and the distal end 82 can be formed along the longitudinal axis L2 (FIG. 4). It should be noted, however, that although the planar bar 52 is described and illustrated herein being planar, the planar bar 52 could include a slope if desired, such that the proximal end 80 is offset from the distal end 82. Further, the planar bar 52 could have any desired shape, such as linear or non-linear, and could be curved between the proximal and distal ends 80, 82 thereof. In addition, if curved, the contoured bar 50 and the planar bar 52 could have substantially similar radii such that one of the contoured bar 50 and the planar bar 52 could pass under the other of the contoured bar 50 and the planar bar 52 during translation of the cross connector system 10, thereby increasing or decreasing the distance D spanned by the contoured bar 50 and the planar bar 52.

In addition, it should be noted that multiple contoured bars 50 and planar bars 52 could be coupled together to span the distance D. In this regard, contoured bars 50 and planar bars 52 could be coupled together in a zig-zag pattern so as to extend diagonally between various portions of the first fixation system 12 and the second fixation system 14 along the length of the spine, if desired. The use of a zig-zag pattern can enable the cross connector system 10 to translate as the contoured bars 50 and planar bars 52 angulate relative to each other. For example, as the zig-zag pattern approaches a linear configuration, the distance D spanned by the cross connector system 10 can increase. The distance D spanned by the cross connector system 10 can decrease as the zig-zag pattern moves toward a non-linear configuration. In another example, planar bars 52 could be coupled together in a zig-zag pattern spanning the distance D between the first fixation system 12 and the second fixation system 14 to enable translation without requiring the use of the contoured bar 50.

Further, one or more of the contoured bars 50 and planar bars 52 could be coupled between the bone engaging members 16 of the first fixation system 12 or the second fixation system 14 in place of the connecting rod 18. Thus, in this example, the contoured bars 50 and planar bars 52 could act to connect the bone engaging members 16 without the use of a connecting rod 18. Therefore, in this example, the bone engaging members 16 could be formed without receiving portions for receipt of the connecting rod 18. Accordingly, any number of contoured bars 50 and planar bars 52 could be employed in any desired configuration to form the cross connector system 10 within the scope of the present teachings.

With reference to FIGS. 2-4, the proximal end 80 and the distal end 82 can each define a bore 84. The bore 84 can receive a portion of the locking system 54 to couple the proximal end 80 and the distal end 82 of planar bar 52 to one of the contoured bar 50, bridge system 56 or rod clamp system 58. As will be discussed, the bore 84 can allow the locking system 54 to move relative to a main axis A of the bore 84. In this regard, the bore 84 can allow the locking system 54 to rotate about the axis A of the bore 84 and pivot or angulate relative to the axis A when the locking system 54 is in a first state (FIG. 2). The bore 84 can have any desired shape, and for example, can be circular, elliptical, polygonal, etc.

With reference to FIG. 3, the bore 84 can have an interior surface 86. The interior surface 86 can be configured to correspond to a portion of the locking system 54, as will be discussed in greater detail herein. In one example, the interior surface 86 can be spherical, however, the interior surface 86 can have any desired profile, such as smooth, spherical, tapered, etc. In addition, if desired, the internal surface 86 can include a maximum angle portion 86a. The maximum angle portion 86a can comprise a portion of the interior surface 86 of the bore 84 that has a reduced cross-section to enable the locking system 54 to pivot or angulate relative to the axis A to another, greater, maximum angle A1 as illustrated in FIGS. 2 and 4.

The locking system 54 can couple the cross connector system 10 together. In this regard, the locking system 54 can be received in the bores 66, 84 and slot 70 to couple the contoured bar 50 to the planar bar 52, and to also couple one or more of the bridge system 56 and rod clamp system 58 to a respective one of the contoured bar 50 and the planar bar 52. With reference to FIG. 3, the locking system 54 can include an expansion ring 90, a first locking device or first fastener 92, a second locking device or second fastener 94 and a mating rail component 96.

With reference to FIGS. 3 and 4, the expansion ring 90 can be received in the bores 66, 84 of the contoured bar 50 and the planar bar 52. The expansion ring 90 can be comprised of any suitable material, such as a biocompatible metal, metal alloy or polymer. In one example, the expansion ring 90 can be composed of a resilient material, which enables the expansion ring 90 to expand and contract based upon the movement of the first fastener 92 or second fastener 94 relative to the expansion ring 90, as will be discussed herein. The expansion ring 90 can be generally annular, and can include a first or exterior surface 98, a second or interior surface 100 and a slot 102.

The first or exterior surface 98 can be configured to mate with the interior surface 68, 86 of each of the bores 66, 84 so that the expansion ring 90 can rotate about the axis A and pivot or angulate relative to the axis A defined by the bores 66, 84 (FIG. 4). Thus, in one example, the exterior surface 98 can be substantially spherical to enable the expansion ring 90 to move, rotate and pivot or angulate within the bores 66, 84 as illustrated in FIGS. 2 and 4. It should be noted that although the exterior surface 98 is illustrated herein as being spherical, the exterior surface 98 can have any desired shape, such as elliptical, cylindrical or generally polygonal. With reference to FIG. 3, the exterior surface 98 can optionally include at least one maximum angle feature 104 and at least one friction portion 106.

The at least one maximum angle feature 104 can be formed along a distalmost or bottom of the exterior surface 98 of the expansion ring 90. In one example, the at least one maximum angle feature 104 can cooperate with the interior surface 68, 86 of the bores 66, 84 to enable the expansion ring 90 to occupy an at least one second greater maximum angle A2. It should be noted that the at least one maximum angle feature 104 can be optional if desired.

The at least one maximum angle feature 104 can enable the locking system 54 to move, pivot or angulate relative to the axis A of the bores 66, 84 to the at least one second maximum angle A2 relative to the axis A. The at least one second maximum angle A2 can have an angle greater than or equal to the at least one first maximum angle A1. In addition, it should be understood that the cross connector system 10 can include both of the maximum angle portion 68a of the bores 66, 84 and the at least one maximum angle feature 104 of the expansion ring 90, or could include one of the maximum angle portion 68a of the bores 66, 84 and the at least one maximum angle feature 104 of the expansion ring 90, or any combination thereof.

If utilized, the at least one friction portion 106 can increase the friction between the expansion ring 90 and the bores 66, 84. The at least one friction portion 106 can comprise any suitable device or technique that can increase the friction between the expansion ring 90 and the bores 66, 84. For example, the at least one friction portion 106 can comprise a coating, mechanical abrasion, machined feature, interference, or chemical etching formed on the exterior surface 98 of the expansion ring 90. Alternatively, at least one friction portion can be composed on the interior surface 68, 86 of the bores 66, 84. It will be understood, however, that the at least one friction portion 106 can be formed on each of the exterior surface 98 of the expansion ring 90 and the interior surface 68, 86 of the bores 66, 84, if desired.

In addition, although the at least one friction portion 106 is described herein as increasing friction, the at least one friction portion 106 can comprise any suitable device or technique that can decrease the friction between the expansion ring 90 and the bores 66, 84. For example, the at least one friction portion 106 can comprise a lubricant coating, a high polished surface, etc., which can decrease the friction between the expansion ring 90 and the bores 66, 84, if desired.

The interior surface 100 can be configured to cooperate with the first fastener 92 and the second fastener 94. In this regard, the interior surface 100 can be configured to match an exterior surface 108 of the first fastener 92 and second fastener 94. In one example, with reference to FIG. 4, the interior surface 100 can be generally uneven or non-uniform in cross section, such that in at least one location, the cross section of the interior surface 100 is greater than a cross section of the interior surface 100 in another location. In other words, the interior surface 100 can comprise a tapered portion 100a, which can transition the interior surface 100 of the expansion ring 90 from a first diameter D1 to a second diameter D2. The transition of the interior surface 100 between the first diameter D1 and the second diameter D2 can cooperate with the exterior surface 108 of the first fastener 92 and the second fastener 94, as will be discussed herein. It should be noted, however, that although the interior surface 100 is illustrated and described herein as having a tapered portion 100a, the interior surface 100 can have a stepped portion or other features that enable the expansion ring 90 to move from a first state to a second state, as will be discussed herein.

The slot 102 can be formed through the expansion ring 90 from a first end 90a to a second end 90b. It should be noted, however, that the slot 102 need not extend from the first end 90a to the second end 90b, but rather, the slot 102 could be formed through only a portion of the expansion ring 90. The slot 102 can enable the expansion ring 90 to move from the first state to the second state. In this regard, in the first state, the expansion ring 90 can be in a relaxed state such that the locking system 54 can be movable relative to the respective one of the contoured bar 50, planar bar 52, bridge system 56 and rod clamp system 58. Thus, when the expansion ring 90 is in the first state, the locking system 54 can be in the first state. In the second state, the expansion ring 90 can be expanded so as to prevent the movement of the locking system 54 relative to the respective one of the contoured bar 50, planar bar 52, bridge system 56 and rod clamp system 58, as will be discussed in greater detail herein. Thus, when the expansion ring 90 is in the second state, the locking system 54 can be in the second state.

It should be noted that the use of the expansion ring 90 is merely exemplary. In this regard, a cam configuration could be employed, in which an oval or elliptically shaped ring is positioned within the expansion ring 90. Movement of the oval or elliptically shaped inner ring from a first position to a second position within the expansion ring 90 can cause the expansion ring 90 to move from the first state to the second state. Furthermore, the expansion ring 90 need not include a slot 102 to enable expansion. Rather, the expansion ring 90 could be formed of a flexible material that allows for expansion, such as a polymeric material. Alternatively, the expansion ring 90 could comprise a coil of material, which could expand during the advancement of the first fastener 92 and second fastener 94. The expansion ring 90 could also have a plurality of partial slots formed about a circumference of the expansion ring 90 to facilitate expansion. Thus, the shape and configuration of the expansion ring 90 is merely exemplary as any device capable of moving from a first unexpanded condition to a second expanded condition could be employed with the cross connector system 10. Further, the first fastener 92 and the second fastener 94 could be configured to have a cam feature, such that movement of the first fastener 92 and the second fastener 94 from a first position to a second position could cause the locking system 54 to move from the first state to the second state.

With reference to FIGS. 3 and 4, the first fastener 92 can have a head 110 and a shank 112. The first fastener 92 can be composed of any desired biocompatible material, and for example, can be composed of a suitable biocompatible metal, metal alloy or polymer. The head 110 can be generally circular, and can include a first or upper portion 114 and a second or lower portion 116. The upper portion 114 can be coupled to the lower portion 116 via a taper T. The upper portion 114 can include a driver engagement feature 114a, which can enable a suitable driver to be coupled to the first fastener 92 to couple the first fastener 92 to a portion of the bridge system 56, as will be discussed further herein. For example, the driver engagement feature 114a can comprise a recessed socket configured to receive a screwdriver, however, it should be understood that any suitable mechanism or technique can be used to couple the first fastener 92 to the portion of the bridge system 56.

With reference to FIG. 4, the upper portion 114 can have a first cross-section C1, which can be different than a cross-section C2 of the lower portion 116. In one example, the first cross-section C1 can be greater than the cross-section C2 of the lower portion 116. In this example, the taper T can couple or transition the upper portion 114 into the lower portion 116. The difference in the cross-section C1 and the cross-section C2 can cooperate with the interior surface 100 of the expansion ring 90 such that the movement of the first fastener 92 relative to the expansion ring 90 can transition the expansion ring 90, and thus, the locking system 54 from the first state to the second state. The lower portion 116 can be adjacent to the shank 112.

With reference to FIG. 3, the shank 112 can include a plurality of threads 112a for coupling the first fastener 92 to a respective one of the bridge system 56 and the rod clamp system 58. It should be noted that although the shank 112 is described and illustrated herein as comprising a plurality of threads 112a, any suitable technique could be used to couple the shank 112 to the bridge system 56 or rod clamp system 58, such as a press-fit, a plurality of tangs, an interference fit, etc. With reference to FIG. 4, the shank 112 can have a length L1. In one example, the length L1 of the first fastener 92 can be shorter than a length L2 of a shank 118 of the second fastener 94.

In this regard, the length L2 of the shank 118 of the second fastener 94 can be long enough to interconnect the contoured bar 50 with the planar bar 52 via the slot 70 and the mating rail component 96. The second fastener 94 can be composed of a suitable biocompatible material, such as a biocompatible metal, metal alloy or polymer. As the second fastener 94 can be similar to the first fastener 92, only the differences between the second fastener 94 and the first fastener 92 will be discussed in great detail herein, and the same reference numerals will be used to denote the same or similar components. The second fastener 94 can include the head 110 and the shank 118.

As discussed, the shank 118 can have the length L2, which can be longer than the length L1 of the shank 112. The shank 118 can also include a plurality of threads 118a for coupling the second fastener 94 to the mating rail component 96. It should be noted that although the shank 118 is described and illustrated herein as comprising a plurality of threads 118a, any suitable technique could be used to couple the shank 118 to the mating rail component 96, such as a press-fit, a plurality of tangs, an interference fit, etc.

With reference to FIGS. 3 and 4, the mating rail component 96 can cooperate with the second fastener 94 and the expansion ring 90 to couple the slot 70 of the contoured bar 50 to the bore 84 of the planar bar 52. The mating rail component 96 can be composed of any suitable biocompatible material, such as a biocompatible metal, metal alloy or polymer. The mating rail component 96 can be coupled to the shank 118 of the second fastener 94 so that the second fastener 94 can move within the slot 70 while the locking system 54 is in the first state, and can be fixed relative to the slot 70 when the locking system 54 is in the second state. Thus, the mating rail component 96 can cooperate with the second fastener 94 to enable the contoured bar 50 to move relative to the planar bar 52 while the locking system 54 is in the first state. In the second state, the mating rail component 96 can cooperate with the second fastener 94 to clamp the contoured bar 50 to the planar bar 52, which can secure or lock the contoured bar 50 to the planar bar 52.

Thus, the mating rail component 96 can comprise any suitable device for coupling the contoured bar 50 to the planar bar 52 via the second fastener 94, and in one example, can include a pair of rails 120 and a bore 122. The pair of rails 120 can extend upwardly from a surface 96a of the mating rail component 96 and can define a generally U-shape for receipt of the distal end 62 of the contoured bar 50. The pair of rails 120 can be spaced apart by a distance about equal to a width of the contoured bar 50 to enable the contoured bar 50 to slide along the surface 96a of the mating rail component 96.

The bore 122 can be formed along a center line of the mating rail component 96 and can extend through the mating rail component 96. In one example, the bore 122 can include a plurality of threads 122a to enable the bore 122 to threadably engage the plurality of threads 118a formed on the shank 118 of the second fastener 94. It should be understood, however, that the bore 122 can be configured as desired to couple the mating rail component 96 to the second fastener 94, and thus, the bore 122 could include mating frictional features, a press-lit interface, adhesives, a plurality of tangs, etc.

With reference to FIGS. 2-4, the bridge system 56 can couple the bone engaging members 16 to the contoured bar 50 and/or the planar bar 52. The bridge system 56 can include a first bridge system 56a and a second bridge system 56b. Each of the first bridge system 56a and the second bridge system 56b can cooperate with the locking system 54 to couple one of the bone engaging members 16 to a respective one of the contoured bar 50 or planar bar 52. It should be noted that although the cross connector system 10 is illustrated herein as including both a first bridge system 56a and a second bridge system 56b, the cross connector system 10 could include only first bridge systems 56a or second bridge systems 56b, if desired.

The first bridge system 56a can include a first bridge 130. The first bridge 130 can be composed out of any suitable biocompatible material, such as a biocompatible metal, metal alloy or polymer. The first bridge 130 can include a first or upper side 132, a second or lower side 134 and a bore 136. The upper side 132 can be positioned adjacent to the expansion ring 90 when the first bridge system 56a is coupled to the locking system 54 (FIG. 4). The lower side 134 can include a first arm 138 opposite a second arm 140. In one example, the first arm 138 and the second arm 140 can be coupled to the lower side 134 via living hinges 142 to enable the first arm 138 and second arm 140 to resiliently engage the bone engaging member 16, however, the first arm 138 and second arm 140 could be directly coupled to the lower side 134 if desired. If the living hinges 142 are employed, the first arm 138 can be spaced a distance apart from the second arm 140, which can be smaller than a width of the saddle 22. This can enable the first bridge 130 to be snap-fit onto the saddle 22.

With reference to FIG. 4, each of the first arm 138 and the second arm 140 can include at least one coupling feature 144. The at least one coupling feature 144 can extend outwardly from an interior surface 138a, 140a of the first arm 138 and the second arm 140 and can be configured to engage the at least one coupling feature 42 formed on the arms 34, 36 of the saddle 22. Generally, the first bridge 130 can be snap fit onto the saddle 22 such that the at least one coupling feature 144 of the first arm 138 and the second arm 140 can snap into the detent defined by the at least one coupling feature 42 of the arms 34, 36. It should be noted that, if desired, the at least one coupling feature 144 could be formed on the arms 34, 36 and the at least one coupling feature 42 could be defined on the first arm 138 and the second arm 140 of the first bridge 130. Once the at least one coupling feature 144 is coupled to the at least one coupling feature 42, the at least one coupling feature 42 can cooperate with the at least one coupling feature 144 to prevent the separation of the first bridge 130 from the saddle 22 by preventing the upward movement of the first arm 138 and second arm 140. As will be discussed, by preventing this upward movement, the at least one coupling feature 144 and the at least one coupling feature 42 can cooperate to strengthen the connection between the first bridge 130 and the saddle 22 by creating a tension loading condition through the tightening of the first fastener 92.

The bore 136 can be formed through the first bridge 130 from the upper side 132 to the lower side 134. The bore 136 can be configured to threadably engage the plurality of threads 112a of the shank 112 of the first fastener 92, and thus, the bore 136 can include a plurality of threads 136a. It should be noted that the bore 136 need not include the plurality of threads 136a, but rather can be press-fit, snap fit, etc. to couple the first bridge 130 to the first fastener 92. In the example of the bore 136 having the plurality of threads 136a, the first fastener 92 can be threaded into engagement with the first bridge 130 after the first bridge 130 is coupled to the saddle 22 to create the tension loading condition, as will be discussed in greater detail herein.

With reference to FIGS. 2-4, the second bridge system 56b can include a second bridge 150 and a screw clamp 152. Each of the second bridge 150 and the screw clamp 152 can be composed out of any suitable biocompatible material, such as a biocompatible metal, metal alloy or polymer. The second bridge 150 can include a first or upper side 154, a second or lower side 156 and a bore 158. The upper side 154 can be positioned adjacent to the expansion ring 90 when the second bridge system 56b is coupled to the locking system 54 (FIG. 4). The lower side 156 can include a first arm 160 opposite a second arm 162. In one example, the first arm 160 and second arm 162 can be directly coupled to or integrally formed with the lower side 156, however, the first arm 160 and the second arm 162 could be coupled to the lower side 156 via living hinges, if desired. Generally, the first arm 160 can be spaced a distance apart from the second arm 162, which can be greater than a width of the saddle 22. This can enable the second bridge 150 to be assembled over the screw clamp 152, such that the screw clamp 152 is substantially surrounded by the second bridge 150, as will be discussed in greater detail herein.

The bore 158 can be formed through the second bridge 150 from the upper side 154 to the lower side 156. The bore 158 can be configured to position the second bridge 150 about the shank 112 of the first fastener 92. Generally, the bore 158 can be unthreaded, but the bore 158 could include a plurality of threads to enable the second bridge 150 to threadably engage the first fastener 92, if desired. If the bore 158 is unthreaded, the size of the bore 158 can be such that the first fastener 92 can rotate relative to the second bridge 150 to enable the screw clamp 152 to be coupled to the first fastener 92.

The screw clamp 152 can cooperate with the second bridge 150 to couple the bone engaging member 16 to the locking system 54. The screw clamp 152 can include a first or upper side 161, a second or lower side 163 and a bore 165. The upper side 161 can be positioned adjacent to the lower side 163 when the second bridge system 56b is coupled to the locking system 54. The lower side 163 can include a first arm 166 opposite a second arm 168. In one example, the first arm 166 and second arm 168 can be directly coupled to or integrally formed with the lower side 163, however, the first arm 166 and the second arm 168 could be coupled to the lower side 163 via living hinges, if desired. Generally, the first arm 166 can be spaced a distance apart from the second arm 168, which can be greater than a width of the saddle 22, but less than the distance defined by the second bridge 150. This can enable the screw clamp 152 to fit about or over the arms 34, 36 of the saddle 22, as will be discussed in greater detail herein.

In addition, with reference to FIG. 4, each of the first arm 166 and the second arm 168 can include at least one coupling feature 169. The at least one coupling feature 169 can extend outwardly from an interior surface 166a, 168a of the first arm 166 and the second arm 168, respectively, and can be configured to engage the at least one coupling feature 42 formed on the arms 34, 36 of the saddle 22. Generally, the screw clamp 152 can be positioned over the saddle 22 such that the at least one coupling feature 169 of the first arm 166 and the second arm 168 can snap into the detent defined by the at least one coupling feature 42 of the arms 34, 36. It should be noted that the at least one coupling feature 169 could be formed on the arms 34, 36, and the at least one coupling feature 42 could be formed on the first arm 166 and the second arm 168.

In addition, it should be noted that the screw clamp 152 can be sized to increase or decrease the amount of tactile feedback provided when the at least one coupling feature 169 engages the at least one coupling feature 42 of the arms 34, 36. In this regard, the screw clamp 152 can be sized smaller than the saddle 22 of the bone engaging member 16 so that a tactile snap is observed when the screw clamp 152 is coupled to the saddle 22. Alternatively, the screw clamp 152 can be sized larger than the saddle 22, so that no tactile snap is observed when the at least one coupling feature 169 engages the at least one coupling feature 42 of the arms 34, 36. Thus, the size and shape of the screw clamp 152 is merely exemplary.

Once the at least one coupling feature 169 is coupled to the at least one coupling feature 42, the at least one coupling feature 42 can cooperate with the at least one coupling feature 169 to prevent the separation of the second bridge system 56b from the saddle 22 by preventing the upward movement of the first arm 166 and second arm 168. As will be discussed, by preventing this upward movement, the at least one coupling feature 169 and the at least one coupling feature 42 can cooperate to strengthen the connection between the second bridge system 56b and the saddle 22 by creating a tension loading condition through the tightening of the first fastener 92. In other words, as the screw clamp 152 moves upward, the second bridge 150 can squeeze the screw clamp 152 inward about the saddle 22 of the first fastener 92.

The bore 165 can be formed through the screw clamp 152 from the upper side 161 to the lower side 163, and can be formed to include an annular rim or lip that extends a distance above the upper side 161 and is sized to be received by the bore 158. The bore 165 can be configured to threadably engage the plurality of threads 112a of the shank 112 of the first fastener 92, and thus, the bore 165 can include a plurality of threads 165a. It should be noted that the bore 165 need not include the plurality of threads 165a, but rather can be press-fit, snap fit, etc. to couple the screw clamp 152 to the first fastener 92. In the example of the bore 165 having a plurality of threads 165a, the first fastener 92 can be threaded into engagement with the screw clamp 152 and can cooperate with the second bridge 150 to create the tension loading condition. The tension loading condition acts to strengthen the connection between the second bridge system 56b and the bone engaging member 16.

With reference to FIGS. 5-8, the rod clamp system 58 can be coupled to the contoured bar 50 (FIG. 8) and/or the planar bar 52 (FIGS. 5 and 8) via the locking system 54. The rod clamp system 58 can receive and be coupled to one of the connecting rods 18, and thus, the rod clamp system 58 operates to couple the connecting rod 18 to the contoured bar 50 and/or planar bar 52. The rod clamp system 58 can be formed of a suitable biocompatible material, such as a biocompatible metal, metal alloy or polymer. The rod clamp system 58 can include a rod bell 170 and a rod clamp 172.

The rod bell 170 can cooperate with the rod clamp 172 to couple the connecting rod 18 to the rod clamp system 58. It should be noted that although the rod clamp 172 is described and illustrated herein as including the rod bell 170, the rod clamp 172 could be employed without the rod bell 170, if desired. With reference to FIG. 7, the rod bell 170 can be bowl or bell shaped, and can define a contact portion 174 at a first end 170a and a bore 176 at a second end 170b. A cavity 178 can be formed from the first end 170a to the second end 170b, which can receive at least a portion of the rod clamp 172, as will be discussed. The contact portion 174 can cooperate with the rod clamp 172 to couple the connecting rod 18 to the rod clamp system 58, as will be discussed in greater detail herein. Briefly, the contact portion 174 can include a generally tapered region that can be configured to contact a portion of the rod clamp 172, which can in turn cause the rod clamp 172 to compress against the connecting rod 18.

Generally, the bore 176 can be formed along a center line of the rod bell 170, which can be substantially parallel with a longitudinal axis L of the rod clamp system 58 (FIG. 7). The bore 176 can enable the rod bell 170 to be positioned about the shank 112 of the first fastener 92. In one example, the bore 176 is unthreaded and sized to enable the first fastener 92 to rotate relative to the bore 176, however, the bore 176 could include a plurality of threads, if desired, to enable the rod bell 170 to be threadably coupled to the first fastener 92. The bore 176 may also receive at least a portion of the rod clamp 172 when the first fastener 92 is coupled to the rod clamp 172 as will be discussed herein.

The cavity 178 can be defined between the contact portion 174 and the bore 176. The cavity 178 can have a diameter greater than a diameter of the bore 176 to enable at least a portion of the rod clamp 172 to be received within the rod bell 170. It should be noted, however, that the connecting rod 18 can have a diameter equal to or less than the diameter of the bore 176, if desired.

The rod clamp 172 can be generally V-shaped, and can be substantially symmetrical about the longitudinal axis L of the rod clamp system 58 (FIG. 7). The rod clamp 172 can include a first clamping arm 180 coupled to a second clamping arm 182 via a base portion 184. The first clamping arm 180 and second clamping arm 182 can be coupled to the base portion 184 so as to define a generally V-shaped channel 186 for receipt of the connecting rod 18. As the rod clamp 172 can be substantially symmetrical about the longitudinal axis L, the first clamping arm 180 can be substantially a mirror image of the second clamping arm 182. In one example, the rod clamp 172 can be configured so as to engage, slide or snap onto the connecting rod 18 prior to the tightening of the rod clamp system 58, which can enable the rod clamp system 58 to stay in place prior to fixedly coupling the rod clamp system 58 to the connecting rod 18. It should be noted, however, that the rod clamp system 58 need not be fixedly coupled to the connecting rod 18, if desired. By not fixedly coupling the rod clamp system 58 to the connecting rod 18, the rod clamp system 58 can move or translate along the connecting rod 18 to assist in preserving motion, for example.

Each of the first clamping arm 180 and the second clamping arm 182 can include a first end 180a, 182a and a second end 180b, 182b. The first end 180a, 182a can include a tapered edge 188 and a concave clamp portion 190, which can each be formed along the channel 186. The tapered edge 188 can assist in guiding the connecting rod 18 into the channel 186. The concave clamp portion 190 can be configured to bear against a surface of the connecting rod 18 to couple the connecting rod 18 to the rod clamp system 58. Generally, the rod clamp 172 can snap onto the connecting rod 18 so that the rod clamp system 58 can stay in place prior to being tightened onto the connecting rod 18.

The second end 180b, 182b can be coupled to the base portion 184. The base portion 184 can define a threaded bore 192, which can be formed from the base portion 184 through the second end 180b, 182b and can terminate adjacent to or at the concave clamp portion 190. The threaded bore 192 can include a plurality of threads 192a, which can cooperate or matingly engage the plurality of threads 112a on the shank 112 of the first fastener 92. The engagement of the first fastener 92 with the threaded bore 192 can draw the first clamping arm 180 and the second clamping arm 182 rearward toward the rod bell 170, which can compress the rod clamp 172 to clamp the connecting rod 18 to the rod clamp system 58, as will be discussed in greater detail herein. It should be noted, however, that the rod clamp system 58 need not include all of the components described herein. For example, a rod clamp system could comprise a single component having a U-shape for receipt of the connecting rod 18 therethrough and threads for mating with the first fastener 92 to couple the single component to the connecting rod 18 and to the cross connector system 10.

In order to employ the cross connector system 10, the first fixation system 12 and the second fixation system 14 can be coupled to the anatomy via any suitable technique (FIG. 1). Briefly, it should be noted that the insertion of the first fixation system 12 and the second fixation system 14 into the anatomy is beyond the scope of the present teachings and need not be described herein. In a conventional manner insofar as the present teachings are concerned, exemplary systems and methods for the insertion of the first fixation system 12 and the second fixation system 14 into the anatomy can include those employed in the Polaris™ 5.5 Spinal System, commercially available from Biomet, Inc. of Warsaw, Ind., or the tools disclosed in commonly owned U.S. Patent Publication No. 2008/0077138, filed on Apr. 20, 2007 and U.S. patent application Ser. No. 13/103,069, filed on May 8, 2011, each of which are incorporated by reference herein. In addition, the first fixation system 12 and the second fixation system 14 need not include all of the components illustrated in FIG. 1, but rather, the bone engaging members 16 could comprise a saddle with threads that engages the anatomy, hooks, etc.

Once the first fixation system 12 and the second fixation system 14 are coupled to the desired portion of the anatomy, the cross connector system 10 can be assembled to bridge the distance D between the first fixation system 12 and the second fixation system 14 to provide additional strength to the construct created by the first fixation system 12 and the second fixation system 14 (FIG. 1). In order to bridge the distance D, various components of the cross connector system 10 can be coupled together as needed, in any desired configuration, according to the patient's anatomy.

In one example, initially, the contoured bar 50 can be assembled to the planar bar 52 using the expansion ring 90, mating rail component 96 and second fastener 94 (FIGS. 2-4). Generally, the contoured bar 50 can be coupled to the planar bar 52 such that the locking system 54 is in the first state and the contoured bar 50 is movable relative to the planar bar 52 (FIG. 2). It should be noted that although the contoured bar 50 and planar bar 52 are described and illustrated herein as being coupled together to span the distance D, two contoured bars 50, two planar bars 52 and combinations thereof could be used to span the distance D. Further, multiple combinations of the first fastener 92 and the second fastener 94 can be used to span the distance D.

Once the combination of contoured bar(s) 50 and planar bar(s) 52 are selected and coupled together, the user can decide how to couple the contoured bar 50 and planar bar 52 to the first fixation system 12 and the second fixation system 14. In this regard, depending upon the anatomy and position of the first fixation system 12 and the second fixation system 14, the user can determine whether to use the first bridge system 56a (FIG. 3), second bridge system 56b (FIG. 3) and/or the rod clamp system 58 (FIG. 5). In one example, a first bridge system 56a and a second bridge system 56b could be used to couple the contoured bar 50 and the planar bar 52 to the first fixation system 12 and the second fixation system 14 (FIG. 2). In another example, one of the first bridge system 56a and the second bridge system 56b can be employed along with a rod clamp system 58 to bridge the distance D (FIG. 5). In another example, two rod clamp systems 58 can be used to couple the contoured bar 50 and the planar bar 52 to the first fixation system 12 and the second fixation system 14 (FIG. 8).

In the example of a first bridge system 56a and a second bridge system 56b, the first bridge system 56a and second bridge system 56b can be coupled to a respective one of the contoured bar 50 and the planar bar 52 (FIG. 2). In order to couple the first bridge system 56a to the respective one of the contoured bar 50 and the planar bar 52, the first bridge 130 can be coupled to the saddle 22 such that the coupling feature(s) 144 engage the coupling feature(s) 42. Then, with the expansion ring 90 coupled to the bore 84, the first fastener 92 can be inserted through the expansion ring 90 so that the first fastener 92 can threadably engage the threads 136a of the bore 136 (FIG. 4). In one example, the first fastener 92 can be at least initially engaged with the bore 136 of the first bridge 130 to enable the first bridge system 56a to be coupled to the contoured bar 50 while allowing the contoured bar 50 to move about the expansion ring 90. Thus, the first bridge system 56a can be coupled to the contoured bar 50 such that the locking system 54 is in the first state.

In the example of FIG. 2, the second bridge system 56b can be coupled to the planar bar 52. First, the screw clamp 152 can be coupled to the saddle 22 such that the coupling features 169 of the screw clamp 152 are engaged with the coupling feature 42 of the saddle 22 (FIGS. 2-4). Then, the second bridge 150 can be positioned about the screw clamp 152. With the expansion ring 90 positioned in the bore 84 of the planar bar 52, the first fastener 92 can be inserted through the expansion ring 90 until the first fastener 92 is at least partially threadably engaged with the threads 152a of the screw clamp 152. Generally, the first fastener 92 can be at least partially engaged with the threads 152a of the screw clamp 152 such that the second bridge system 56b is coupled to the planar bar 52, but the locking system 54 is in the first state. With the locking system 54 in the first state, the planar bar 52 can be movable relative to the second bridge system 56b to enable the user to position the planar bar 52 as desired within the patient's anatomy (FIG. 2).

Once the contoured bar 50 and the planar bar 52 are positioned as desired within the anatomy, the locking system 54 can be moved from the first state to the second state. In this regard, the first fastener 92 can be rotated further into engagement with the first bridge system 56*a* and second bridge system 56*b* until the tapered portion T of the first fastener 92 abuts the tapered portion 100*a* of the expansion ring 90 (FIGS. 3 and 4). The advancement of the first fastener 92 within the bore 136 of the first bridge system 56*a* can cause the tension loading condition. In this regard, the advancement of the first fastener 92 within the bore 136 can cause the first fastener 92 to contact and push down on the plug 38 secured within the saddle 22 of the bone engaging member 16. The downward application of force by the first fastener 92 on the plug 38 in combination with the upward application of force caused by the engagement of between the coupling feature(s) 144 and the coupling feature(s) 42 can cause this tension loading condition.

The contact between the tapered portions T, 100*a* can cause the expansion ring 90 to expand from the first state to a second state, thereby frictionally locking the contoured bar 50 relative to the first fastener 92 and the first bridge system 56*a*. Thus, the locking system 54 in the second state can frictionally lock the contoured bar 50 relative to the first bridge system 56*a*.

In addition, it should be noted that although the locking system 54 is described herein as moving from a first state to a second state, the locking system 54 could be positioned in a middle, third state if desired. In this regard, in the middle state, the first fastener 92 and/or second fastener 94 can be tightened, but not tightened enough to cause the expansion ring 90 to expand from the first state to the second state. In this third state, the friction between the first fastener 92 and/or second fastener 94, the expansion ring 90 and the contoured bar 50 and/or planar bar 52 has increased, thereby forming a "friction fit" between the components. This "friction fit" can allow the surgeon to manipulate the cross connector system 10 to a desired position and have the cross connector system 10 remain in that position. Thus, the middle state can enable the surgeon to evaluate the positioning of the cross connector system 10 prior to moving the locking system 54 to the second state.

In order to lock the contoured bar 50 relative to the planar bar 52, the second fastener 94 can be threaded further into engagement with the mating rail component 96 until the tapered portion T of the second fastener 94 abuts the tapered portion 100*a* of the expansion ring 90 (FIGS. 3 and 4). As discussed, the contact between the tapered portions T, 100*a* can cause the expansion ring 90 to expand from the first state to a second state, thereby frictionally locking the contoured bar 50 relative to planar bar 52. Thus, with the locking system 54 in the second state, the contoured bar 50 can fixedly coupled to the planar bar 52.

To lock the planar bar 52 relative to the second bridge system 56*b*, the first fastener 92 can be threadably advanced within the bore 165 of the screw clamp 152. The advancement of the first fastener 92 relative to the screw clamp 152 can cause the tension loading condition. In addition, the advancement of the first fastener 92 can cause contact between the tapered portion T of the first fastener 92 and the tapered portion 100*a* of the expansion ring 90 (FIGS. 3 and 4). As discussed, the contact between the tapered portions T, 100*a* can cause the expansion ring 90 to expand from the first state to a second state, thereby frictionally locking the planar bar 52 relative to the second bridge system 56*b*. Thus, the locking system 54 in the second state can frictionally lock the contoured bar 50 relative to the second bridge system 56*b*.

In the case of the cross connector system 10 that includes one or more rod clamp systems 58, such as that illustrated in FIGS. 5-8, the rod clamp 172 can be positioned within the rod bell 170, and the first fastener 92 can be inserted into the threaded bore 192 to initially couple the rod clamp system 58 to the respective one of the contoured bar 50 and planar bar 52 (FIG. 6). Thus, the rod clamp system 58 can be coupled to the contoured bar 50 or planar bar 52 such that the contoured bar 50 or planar bar 52 can be movable relative to the rod clamp system 58 (FIG. 8). Then, the rod clamp 172 can be positioned on or about the connecting rod 18 such that the concave clamp portions 190 are adjacent to a surface of the connecting rod 18. Once the contoured bar 50 and/or planar bar 52 are positioned as desired relative to the anatomy, the first fastener 92 can be threadably advanced within the bore 194 and the rod clamp 172 can be compressed until the concave clamp portions 190 are coupled to the connecting rod 18 (FIG. 7). The further advancement of the first fastener 92 can also cause the tapered portion T of the first fastener 92 to contact the tapered portion 100*a* of the expansion ring 90. The contact between the tapered portions T, 100*a* can cause the expansion ring 90 to move from the first state to the second state, thereby causing the locking system 54 to move from the first state to the second state. In this second state, the contoured bar 50 or planar bar 52 can be fixedly coupled to the rod clamp system 58.

Accordingly, the cross connector system 10 can be available as a kit, which can be used to strengthen a construct formed by two spinal fixation systems. It should be noted, however, that the cross connector system 10 could be provided in various assemblies from which a surgeon could select for the particular patient specific application. The various components of the cross connector system 10 can be customized to fit the particular anatomy and construct created for the patient. In addition, by including the first bridge system 56*a*, second bridge system 56*b* and rod clamp system 58 the surgeon can decide the best connection point for the cross connector system 10. Further, by enabling the contoured bar 50 and planar bar 52 to move relative to each other and relative to the bridge system 56 and rod clamp system 58, the cross connector system 10 can be positioned in various different locations within the anatomy to enable optimization of the location of the cross connector system 10.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A cross-connector system for use during a spinal fixation procedure comprising:
   at least one coupling device defining a coupling bore and having a pair of downwardly extending arms adapted to be coupled to a rod or a bone engaging member;

a contoured bar having a first end offset from a second end, the first end defining a bore having a central axis and the second end defining a slot;

an expansion ring received within the bore of the contoured bar, the expansion ring including a slot configured to expand the expansion ring in a circumferential direction;

a locking device received through the expansion ring and the coupling bore for coupling the at least one coupling device to the contoured bar, the locking device operable in a first state in which the contoured bar is movable about the central axis of the bore and in a second state in which the contoured bar is fixed relative to the central axis of the bore so as to fixedly couple the contoured bar to the at least one coupling device; and a planar bar having a first end and a second end, the first end of the planar bar coupled to the slot to enable relative movement between the contoured bar and the planar bar.

2. The system of claim 1, wherein at least one of the pair of downwardly extending arms includes a coupling feature adapted to engage a portion of the bone engaging member.

3. The system of claim 1, wherein the first end of the planar bar defines a second bore, and the system further comprises:

a second expansion ring received within the second bore of the planar bar;

a mating component defining a pair of rails configured to slidably receive the second end of the contoured bar and a throughbore; and a second locking device received through the second expansion ring, the slot and coupled to the mating component such that in a first state the planar bar and contoured bar are movable relative to each other and in a second state, the planar bar and contoured bar are fixed relative to each other.

4. The system of claim 3, wherein the at least one coupling device comprises a first bridge and a second bridge, the first bridge coupled to the contoured bar and the second bridge coupled to the second end of the planar bar.

5. The system of claim 4, wherein the planar bar defines a third bore having a central axis and the system further comprises:

a third expansion ring received within the third bore of the planar bar; and a third locking device received through the third expansion ring, the third locking device operable in the first state in which the planar bar is movable about the central axis of the third bore and in a second state in which the planar bar is fixed relative to the central axis of the third bore so as to fixedly couple the planar bar to the second bridge.

6. The system of claim 3, wherein the planar bar defines a third bore having a central axis and the system further comprises:

a rod clamp system having a second coupling bore, the rod clamp system adapted to be coupled to a connecting rod;

a third expansion ring received within the third bore of the planar bar; and a third locking device received through the third expansion ring and into the second coupling bore, the third locking device operable in the first state in which the planar bar is movable about the central axis of the third bore and in a second state in which the planar bar is fixed relative to the central axis of the third bore so as to fixedly couple the planar bar to the rod clamp system.

7. The system of claim 6, wherein the rod clamp system further comprises:

a rod bell having a first end opposite a second end, the second end positionable adjacent to the third expansion ring when the rod clamp system is coupled to the planar bar and defining a throughbore to enable the third locking device to pass through the rod bell, the rod bell defining a contact surface at the first end and a cavity that extends from the first end to the second end;

a rod clamp having a first clamping arm coupled to a second clamping arm via a base portion, the first clamping arm and the second clamping arm defining clamping surfaces adapted to couple the connecting rod to the rod clamp system, the base portion defining a fourth bore for receipt of the third locking device, and wherein the movement of the third locking device within the fourth bore causes the locking system to move from the first state to the second state and the first clamping arm and second clamping arm to be compressed towards each other by the contact surfaces of the rod bell.

8. The system of claim 1, wherein the expansion ring is rotatable and pivotable about the central axis of the bore, with the bore having an inner surface defining a first feature that cooperates with the expansion ring to define a maximum pivot angle.

9. The system of claim 1, wherein the expansion ring has an exterior surface that includes a feature that cooperates with the bore to define a maximum pivot angle.

10. The system of claim 1, wherein the locking device comprises a threaded fastener.

11. The system of claim 1, wherein the at least one coupling device comprises a clamp and the pair of downwardly extending arms are adapted to couple to a saddle of the bone engaging member, and the cross-connector system further comprises a bridge having a throughbore configured to align with the coupling bore of the clamp.

12. The system of claim 1, wherein the at least one coupling device comprises a bridge and the pair of downwardly extending arms are adapted to couple to a saddle of the bone engaging member.

13. The system of claim 1 wherein the at least one coupling device comprises a rod clamp and the pair of downwardly extending arms are adapted to engage the rod.

14. A cross-connector system for use during a spinal fixation procedure comprising:

a rod bell defining a throughbore and having a downwardly extending contact portion;

a rod clamp having a coupling bore and a first pair of downwardly extending arms, the rod clamp positionable adjacent to the rod bell such that the throughbore of the rod bell is aligned with the coupling bore of the rod clamp, the rod clamp being adapted to be coupled to a first rod via the first pair of downwardly extending arms;

at least one bar having a first end defining a bore;

an expansion ring received within the bore of the bar, the expansion ring having an expandable outer perimeter; and a locking device received through the expansion ring, the throughbore of the rod bell and the coupling bore of the rod clamp for coupling the rod clamp and the rod bell to the bar.

15. The system of claim 14, wherein the at least one bar comprises a first bar having the first end that defines the bore and a second bar, the first bar having a second end coupled to the second bar.

16. The system of claim 15, wherein a second end of the second bar defines a second bore having a central axis, the system further comprising:
a second expansion ring received within the second bore of the second bar;
a second locking device received through the second expansion ring and into a second coupling bore of a coupling device, the second locking device operable in a first state in which the second bar is movable about the central axis of the second bore and in a second state in which the second bar is fixed relative to the central axis of the second bore so as to fixedly couple the second bar to the coupling device.

17. The system of claim 16, wherein the coupling device comprises a rod clamp system coupled to the second coupling bore.

18. A cross-connector system for use during a spinal fixation procedure comprising:
a first coupling device defining a first coupling bore and having a first pair of downwardly extending arms adapted to be coupled to a first rod;
a second coupling device defining a second coupling bore and having a second pair of downwardly extending arms adapted to be coupled to a second rod;
a linkage system having a first end defining a first bore and a second end defining a second bore;
a first expansion ring received within the first bore of the linkage system;
a second expansion ring received within the second bore of the linkage system;
a first locking device received through the first expansion ring and the first coupling bore of the first coupling device to couple the first coupling device to the first end of the linkage; and
a second locking device received through the second expansion ring and the second coupling bore of the second coupling device to couple the second coupling device to the second end of the linkage;
wherein the first and second coupling devices are each pivotable relative to the linkage system.

19. The system of claim 18, wherein the linkage system further comprises:
a contoured bar having the first end defining the first bore and a second end defining a slot;
a planar bar having the second end defining the second bore and a first end defining a third bore;
a third expansion ring received within the third bore of the planar bar;
a mating component defining a pair of rails configured to slidably receive the second end of the contoured bar and a throughbore; and
a third locking device received through the third expansion ring, the slot and coupled to the mating component such that in a first state the planar bar and contoured bar are movable relative to each other and in a second state, the planar bar and contoured bar are fixed relative to each other.

20. The system of claim 19, wherein the third locking device is different than the first locking device and second locking device.

21. The system of claim 18, wherein the first coupling device and the second coupling device each comprise:
a rod clamp system comprising a rod clamp including one of the first and second coupling bores;
wherein the first and second downwardly extending arms are adapted to be coupled directly to the first and second rods, respectively.

22. The system of claim 21, wherein:
each rod clamp system further comprises a rod bell including one of first and second throughbores, and
the first and second throughbores are aligned with the first and second coupling bores, respectively.

23. The system of claim 18, wherein the first coupling device and the second coupling device each comprise:
a bridge assembly comprising:
a clamp including one of the first and second coupling bores; and
a bridge including one of first and second throughbores;
wherein the first and second throughbores are aligned with the first and second coupling bores, respectively; and
the first and second pairs of downwardly extending arms are adapted to engage saddles of bone engaging members that receive the first and second rods, respectively.

24. The system of claim 18, wherein the first coupling system and the second coupling system each comprise:
a bridge including one of the first and second coupling bores; and
the first and second pairs of downwardly extending arms are adapted to engage saddles of bone engaging members that receive the first and second rods, respectively.

* * * * *